United States Patent
Shi et al.

(10) Patent No.: US 8,257,827 B1
(45) Date of Patent: Sep. 4, 2012

(54) SILICONE COMPOSITION AND DEVICES INCORPORATING SAME

(75) Inventors: Frank Shi, Irvine, CA (US); Ralph Clayman, Irvine, CA (US); Michael K. Louie, Irvine, CA (US); Yeong-Her Lin, Irvine, CA (US); Yuan-Chang Lin, Kaohsiung (TW)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/151,704

(22) Filed: Jun. 2, 2011

(51) Int. Cl.
*B32B 5/16* (2006.01)
(52) U.S. Cl. .................. 428/328; 524/403
(58) Field of Classification Search .......... 428/328; 524/403
See application file for complete search history.

(56) References Cited

U.S. PATENT DOCUMENTS

| | | | |
|---|---|---|---|
| 3,983,879 A | | 10/1976 | Todd |
| 4,061,609 A | * | 12/1977 | Bobear .............. 524/703 |
| 4,311,739 A | * | 1/1982 | Hardman et al. ......... 427/387 |
| 4,581,390 A | | 4/1986 | Flynn |
| 4,838,876 A | | 6/1989 | Wong et al. |
| 4,849,223 A | | 7/1989 | Pratt et al. |
| 4,906,466 A | | 3/1990 | Edwards et al. |
| 5,359,113 A | * | 10/1994 | Bank .............. 556/479 |
| 5,503,840 A | | 4/1996 | Jacobsen et al. |
| 5,522,801 A | | 6/1996 | Wang |
| 5,762,996 A | | 6/1998 | Lucas et al. |
| 5,795,332 A | | 8/1998 | Lucas et al. |
| 6,136,156 A | * | 10/2000 | El-Shall et al. ........ 204/157.41 |
| 6,596,401 B1 | | 7/2003 | Terry et al. |
| 6,743,831 B2 | | 6/2004 | Olsen |
| 6,822,034 B2 | * | 11/2004 | Hanke et al. ............ 524/439 |
| 7,029,755 B2 | | 4/2006 | Terry et al. |
| 7,718,748 B2 | * | 5/2010 | Veit et al. .............. 528/15 |
| 2002/0122832 A1 | * | 9/2002 | Hanke et al. ............ 424/618 |
| 2003/0198821 A1 | | 10/2003 | Terry et al. |
| 2003/0199630 A1 | | 10/2003 | Olsen |
| 2004/0198864 A1 | | 10/2004 | Olsen |
| 2007/0054080 A1 | * | 3/2007 | Hulteen et al. ............ 428/40.1 |
| 2010/0035047 A1 | * | 2/2010 | Ajayan et al. ............ 428/328 |
| 2010/0137472 A1 | | 6/2010 | Ou-Yang |

OTHER PUBLICATIONS

Technical Data Brochure—Shin Etsu Silicone DM-Fluid, Performance Test Results, 2005.*
Slawson, et al., "Bacterial interactions with silver", Biol.of Metals (1990) 3: 151-154, (4 pages).
Samuel, et al., "Prevention of catheter-related infections: the potential of a new nano-silver impregnated catheter," International Journal of Antimicrobial Agents, (2004) 23S1: 75-78 (4 pages).

(Continued)

*Primary Examiner* — James J Seidlick
*Assistant Examiner* — Peter A Salamon
(74) *Attorney, Agent, or Firm* — Vista IP Law Group LLP

(57) ABSTRACT

A silicone composition having anti-microbial properties contains well distributed silica and nanoparticles of a noble metal. Silica and nanoparticles of a noble metal are added to liquid vinyl-terminated polydimethylsiloxane. A coupling agent is then added to the mixture and heated, the coupling agent comprising trialkoxysilane having a formula $R^1Si(OR^2)_3$, wherein $R^1$ is vinyl or allyl, and $R^2$ is an alkyl radical having from 1 to 3 carbon atoms. In one embodiment, trimethylsiloxy terminated polymethylhydrosiloxane is then added to the mixture and heated in the presence of a catalyst so as to cross-link and cure the same into a silicone elastomer. In another embodiment, in place of the trimethylsiloxy terminated polymethylhydrosiloxane, a peroxide is added to mixture and heated to form the silicone. In this later example, no catalyst is needed.

17 Claims, 6 Drawing Sheets

OTHER PUBLICATIONS

Suska, et al., "In vivo evaluation of noble metal coatings," Journal of Biomedical Materials Research Part B: Applied Biomaterials (2009) 92: 86-94, (9 pages).

Scierholz, et al., "Anitiinfective and encrustation-inhibiting materials—myth and facts," International Journal of Antimicrobial Agents, (2002) 19: 511-516 (6 pages).

Furno, et al., "Silver nanoparticles and polymeric medical devices: a new approach to prevention of infection?", Journal of Antimicrobial Chemotherapy, (2004) 54: 1019-1024 (6 pages).

Khorsravi, et al, "In Vitro and in Vivo encrustation and biocompatability testing of materials suitable for articicial bladder construction," University of California, Irvine Poster submitted at World Congress of Endourology (2008) (1 page).

\* cited by examiner

The mechanism of surface treatment a schematic diagram of the solution of first component

SILICONE COMPOSITION AND DEVICES INCORPORATING SAME

FIELD OF THE INVENTION

The field of the invention generally relates to silicone compositions and in particular silicone compositions having anti-encrustation and/or anti-biofilm capabilities. The silicone may be incorporated into medical devices that are used in animal or mammalian body.

BACKGROUND OF THE INVENTION

Silicone mixtures with polyurethane have been used since the 1960's to create urological implantable devices. Before that, latex and other rubber type mixtures have been used to mold into urinary catheters or other medical tubing. Besides coatings and proprietary ratios of silicone and polyurethane, there has been very little change in the substance(s) used for these types of catheters. There is a need for alternative silicone compositions that provide anti-microbial resistance. Anti-microbial resistance may refer to the tendency or ability of the silicone to prevent or mitigate encrustation or blockage of a catheter. Further, anti-microbial resistance may refer to the tendency or ability of the silicone to resist having cellular or biological buildup on the device (e.g., anti-biofilm properties). There is a need for such a composition and devices using the same because of the prevalence of nosocomial infections. The U.S. Center for Disease Control has attributed nosocomial infections as a leading cause of deaths after heart disease, cancer, and stroke. Many of these infections are due to indwelling medical devices such as catheters.

While silicone has particular applications for urinary catheters, anti-microbial silicone based materials are needed to prevent infections of medical devices in other applications. For example, medical devices that utilize silicone is include catheters, diaphragms and seals in dialysis equipment, brain surgery-related products, cosmetic and repair parts, heart surgery-related cardiopulmonary bypass pump tubes, chest tubes, membrane artificial lung products, digestive rubber tubing, duodenal tubing, double-lumen intestinal tubing, feeding tubing, gastric decompression tubes, gastric fistula, gastric lavage tubing, enema tubing, abdominal surgery and reproduction related peritoneal dialysis devices, peritoneal drainage tubes and related devices.

Silicone is increasingly become the material of choice for medical devices because of the relatively recent discovery that the plasticizer agent in the most widely used medical material PVC (used for blood bags, drip tubes, dialysis catheters, etc.) can dissolve in the human body, which puts child-bearing women, newborns, premature children, dialysis patients and processing intensive care unit patients at potential exposure risk. Non-PVC materials such as silicone do not have this particular problem.

Silicone-based materials have unique advantages over many other materials and have been widely used for medical device applications, but they are not intrinsically anti-microbial. A known solution for imparting anti-microbial properties in silicone is to apply a surface coating of silver to a base silicone material. Silver is known for centuries as having active anti-microbial properties. For example, small silver particles (e.g., nanoparticles) can be coated on the exterior surface of silicone. The coating of silver on the exterior surface of silicone adds additional process steps and thus increases the overall cost of the silicone manufacturing process.

Attempts have been made to incorporate silver particles within the silicone material. Due to the large surface area of silver nanoparticles, the nanoparticles will tend to aggregate to reduce the total surface energy. Thus, most of the nanoparticles dispersed in polymers will concentrate or aggregate in certain regions of the silicone polymer and will not be uniformly distributed therein. Furno et al. has demonstrated that silver nanoparticles can be embedded within silicone by using super critical carbon dioxide to impregnate silicone with silver. See Furno et al., Silver nanoparticles and polymeric medical devices: a new approach to prevention infection?, Journal of Antimicrobial Chemotherapy, 54, 1019-1025 (2004). While some antimicrobial activity was observed in the silicone produced by the process of Furno et al., the silver nanoparticles were quickly washed out of the elastomer. Silicone thus formed in this fashion would not be suitable for medical devices because the anti-microbial effects would quickly be washed away once exposed to bodily tissues.

SUMMARY

In one aspect of the invention, a silicone composition is disclosed that includes anti-microbial properties. The silicone composition contains noble metal (e.g., silver) nanoparticles that are well dispersed throughout. The silicone composition is made by using the fact that the inorganic particle surface covered with vinyl groups can be uniformly distributed inside liquid vinyl siloxane, and by a proper surface treatment of the silica (e.g., fumed silica) and the silver nanoparticles first in liquid vinyl siloxane before adding hydride siloxane and a catalyst for the addition-reaction. The surface of the cured silicone composite will then be well-distributed with noble metal nanoparticles. This method can reduce the cost of manufacturing antimicrobial silicone-based medical devices compared with conventional surface-coating processes. These materials have been tested both in vitro and in vivo and perform better than commercially available material. The method of making anti-microbial silicone materials may be used for medical device applications in a variety of physical forms, from coating fluids, to viscoelastic compounds, and cross-linked elastomers.

In one embodiment, a method of forming silicone having anti-microbial properties includes: (a) adding silica and nanoparticles of a noble metal to liquid vinyl-terminated polydimethylsiloxane; (b) adding a coupling agent to the mixture of (a) and heating the same, the coupling agent comprising trialkoxysilane having a formula $R^1Si(OR^2)_3$, wherein $R^1$ is vinyl or allyl, and $R^2$ is an alkyl radical having from 1 to 3 carbon atoms; and (c) adding trimethylsiloxy terminated polymethylhydrosiloxane to the mixture of (b) and subjecting the mixture to heat in the presence of a catalyst so as to cross-link and cure the same into a silicone elastomer.

In another embodiment, a method of forming silicone having anti-microbial properties includes: (a) adding silica and nanoparticles of a noble metal to liquid vinyl-terminated polydimethylsiloxane; (b) adding a coupling agent to the mixture of (a) and heating the same, the coupling agent comprising trialkoxysilane having a formula $R^1Si(OR^2)_3$, wherein $R^1$ is vinyl or allyl, and $R^2$ is an alkyl radical having from 1 to 3 carbon atoms; and (c) adding a peroxide to the mixture of (b) and subjecting the mixture to heat so as to cross-link and cure the same into a silicone elastomer.

In yet another embodiment, a composition of matter includes silicone containing therein a substantially uniform distribution of silica and nanoparticles of a noble metal, wherein the nanoparticles are substantially retained inside the silicone upon exposure of the silicone to fluid.

DETAILED DESCRIPTION OF THE INVENTION

Figure 1:
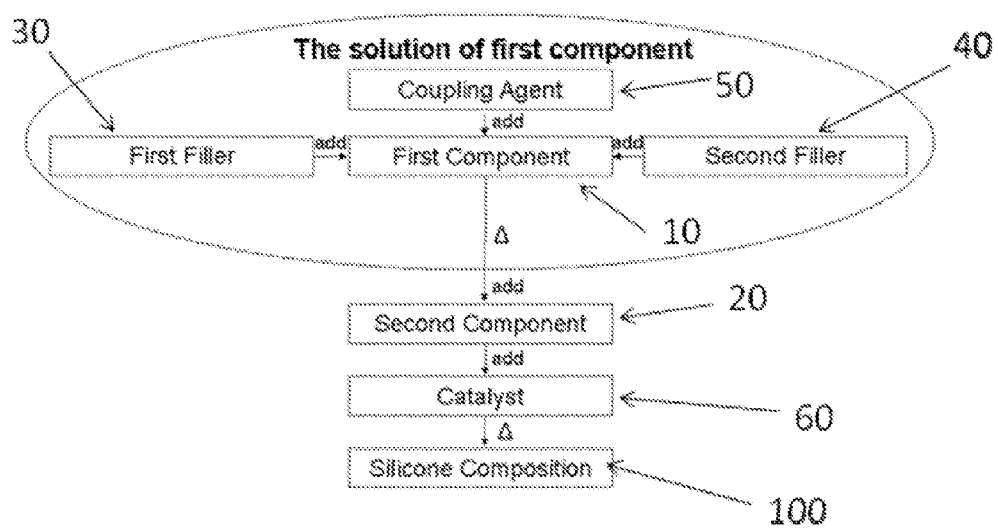
FIG. 1 illustrates a process flow for the addition reaction that produces the silicone composition according to one embodiment.

The silicone material 100 described herein may be used in medical devices including but not limited to catheters, diaphragms, seals in dialysis equipment, brain surgery-related products, cosmetic and repair parts, heart surgery-related products, medical tubing, and the like. The silicone can be used in devices specifically designed for urinary tract implantation or deployment. The devices include, by way of example, ureteral stents, urinary bladder catheters, nephrostomy tubes, and even possibly an artificial urinary bladder/reservoir. The devices may be used to treat various urologic diseases states or processes including, but not limited to: ureteral stricture or stenosis, bladder outlet obstruction, urethral reconstruction, urethral stricture or stenosis, atonic or neurogenic bladder, post-operative drainage after ureteral or renal pelvic reconstruction, kidney stone disease, and urinary tract infection necessitating drainage. The silicone formulation may be used in molds, extruded, or otherwise processed into useful shapes or sizes.

In one embodiment, the silicone composition is made by the addition reaction. A first component 10, vinyl-terminated polydimethylsiloxane [CAS 68083-19-2], forms the base polymer for this reaction. The molecular weight of the first component is between 6,000 and 43,000. The viscosity of this first component 10 is within the range between 100 and 3,500 cSt. A second component 20 of the silicone, methylhydrosiloxane-dimethylsiloxane copolymer [CAS 68037-59-2], is generally with 15-50 mole percentage of methylhydrosiloxane. It served as a cross-linking agent, because the hydride containing siloxanes can react with vinyl coating siloxanes. The molecular weight of the second component 20 is less than 2,000 and generally within the range of 900 to 1,200. The viscosity of the second 20 component is less than 35 cSt and generally within the range of 10 to 15 cSt. Both the first component 10 and second component 20 are liquid containing no more than 10 ppm (parts by weight per million) each of sodium, potassium, iron, copper, lead, and chlorine and no more than 1 ppb (parts by weight per billion) each of uranium and thorium.

The silicone composition includes a first filler 30 which is fumed silica and/or structurally modified silica. The first filler 30 has a diameter within the range of 1 to 2000 nanometers and is used largely for reinforcement. The first filler 30 can be uniformly distributed inside the first component 10, liquid vinyl siloxane. An exemplary first filler 30 includes fumed silica, with specific surface area, BET 220, product Aerosil R812S, sold by Evonik Degussa GmbH. The concentration of the first filler 30 is less than 20% of the total weight of all components and fillers for the silicone composition. The silicone composition also includes a second filler 40 that includes nanoparticles of noble metals (e.g., gold, silver, platinum and palladium) with a diameter within the range of 10 to 200 nanometers. The nanoparticles have anti-microbial functionality and prevent biofilm growth. The concentration of the second filler 40 is less than 1000 ppm of the total weight of all components and fillers for the silicone composition. An exemplary second filler 40 includes silver nanoparticles having an average size of about 150 nanometers (product 47MN-0001) sold by Inframat Corporation, Manchester, Conn.

FIG. 1 illustrates a process flow for the addition reaction that produces the silicone composition according to one embodiment. As seen in FIG. 1, the first component 10, the first filler 30, and the second filler 40 are mixed together. A coupling agent 50, trialkoxysilane, is added for the surface treatment of the first filler 30 and the second filler 40 after the first component 10 is mixed with the first filler 30 and the second filler 40. An exemplary coupling agent 50 includes allyltrimethoxysilane having a viscosity of 5 cSt and molecular weight 162 [CAS 2551-83-9]. The first filler 30 and the second filler 40 may be combined with the first component 10 at the same time—no particular order of addition is needed. The concentration of coupling agent 50 is typically less than 5% of the total weight of all components and fillers for the silicone composition. The trialkoxysilane coupling agent 50 is in the formula $R^1Si(OR^2)_3$, wherein $R^1$ is vinyl or allyl, and $R^2$ is an alkyl radical having from 1 to 3 carbon atoms. Examples include, for instance, vinyl trimethoxysilane, vinyltriethoxysilane, vinyl tributoxysilane, allyl trimethoxysilane, or allyl triethoxysilane. In the surface treatment of the first filler 30 and the second filler 40, the alkoxy groups of the trialkoxysilanes, $R^1Si(OR^2)_3$, are hydrodyzed to form silanol-containing species, $R^1Si(OH)_3$. These silanol-containing species then hydrogen bond with OH group on the first filler 30 and the second filler 40. During curing, a covalent linkage is formed with the surface of the first filler 30 or the second filler 40, due to concomitant loss of water. Hence, the surfaces of the first filler 30 and the second filler 40 were covered with reactive $R^1$ groups (e.g. vinyl or allyl).

Figure 2:
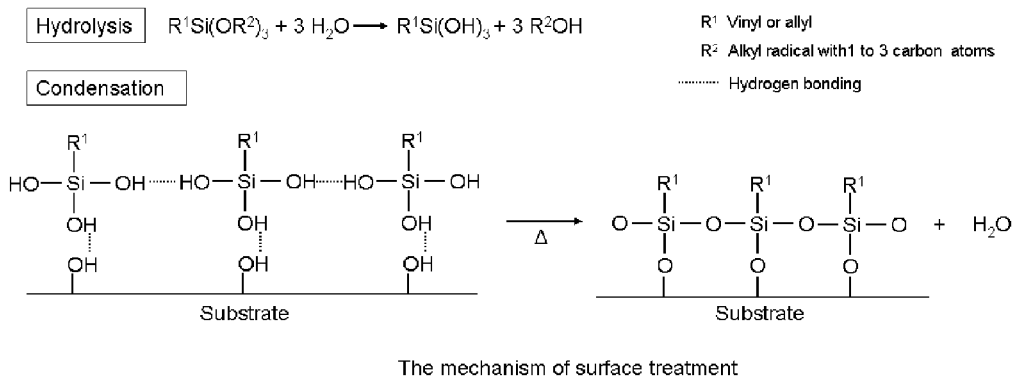
FIG. 2 illustrates the mechanism and surface treatment of the silica and/or nanoparticles.
Figure 3:
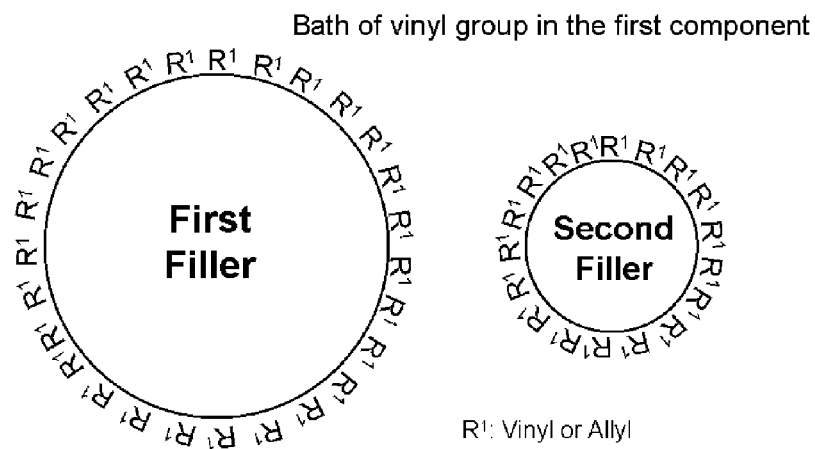
FIG. 3 illustrates a schematic representation of a solution containing the silica and nanoparticles.

FIG. 2 shows the mechanism of surface treatment. The substrate, shown in FIG. 2, is the first filler 30 or the second filler 40. The first filler 30 and second filler 40, covered with vinyl or allyl group, will be well-distributed in the solution of first component 10, due to vinyl containing of first component 10. FIG. 3 shows a schematic diagram of the solution of first component 10. All fillers 30, 40 are covered with $R^1$ group in the bath of vinyl group.

Referring back to FIG. 1, after the coupling agent 50 has been added to the mixture containing the first component 10, the first filler 30, and the second filler 40, the solution is heated. The solution is heated to a temperature with a range of about 100° C. to about 150° C. for several hours. The higher the temperature, the shorter the required time.

As seen in FIG. 1, the second component 20, hydride siloxane, is then added to the solution containing the first component 10, the first filler 30, the second filler 40, and the coupling agent 50. An exemplary second component 20 includes trimethylsiloxy terminated (50% methylhydrosiloxane)-dimethylsiloxane copolymer [CAS 68037-59-2], with a viscosity between 10 and 15 cSt, and molecular weight 900 to 1,200. The hydride (in the second component 20) and the vinyl (in the first component 10 and coupling agent 50) are mixed generally within a range of 1.3:1 to 4.5:1 on a molar ratio basis.

A catalyst 60 is used for the addition reaction of silicone composition, after the mixture has been well mixed. The catalyst 60 is preferably a metal from the group consisting of the platinum metals or a compound or a complex from the group consisting of the platinum metals. Examples of such catalysts 60 are metallic and finely divided platinum, which may be present on a support substrate such as silica, alumina or active carbon, compounds or complexes of platinum such as platinum halides, e.g. $PtCl_4$, $H_2PtCl_6 \cdot 6H_2O$, $Na_2PtCl_4 \cdot 4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6 \cdot 6H_2O$ and cyclohexanone, platinum-vinylsiloxane complexes, such as platinum-1,3-divinyl-1,1,3,3-tetramethyldisiloxane complexes with or without a content of detectable inorganically bonded halogen, bis(gamma-picolinyl) platinum dichloride, tetramethylenedipyridylplatinum dichloride, dicyclopentadienylplatinum dichloride, dimethylsulfoxyethyleneplatinum(II) dichloride, cyclooctadienylplatinum dichloride, norbornadienylplatinum dichloride, gamma-picolinylplatinum dichloride, cyclopentadienylplatinum dichloride, and reaction products of platinum tetrachloride with olefin and primary amine or secondary amine or primary and secondary amine, such as the reaction product of platinum tetrachloride dissolved in 1-octene with secbutylamine or ammonium-platinum complexes. The catalyst is preferably used in amounts of from 5 to 100 ppm by weight calculated in each case as elemental platinum and based on the total weight of all components and fillers for the silicone composition.

With the presence of the catalyst 60, the solution is heated to cure the silicone composition. An exemplary catalyst 60 includes 3-3.5 wt % of Platinum, 1,3-diethenyl-1,1,3,3-tetramethyldisiloxane complexes in vinyl terminated polydimethylsiloxane [Product SIP 6830.3, CAS 68478-92-2] sold by Gelest Inc., Morrisville, Pa. The mixture is heated to a temperature within the range of about 130° C. to about 180° C. for about one to three hours.

The coupling agent 50, containing vinyl or allyl, can react with the second component 20 in the addition-reaction. After the surface treatment of the first filler 30 and the second filler 40, all surfaces of fillers will be covered with the vinyl or allyl (see, e.g. FIG. 3). These fillers 30, 40 will be well-dispersed in the solution of first component 10, and reacted with the second component 20 uniformly. When the silicone composition contains large amount of the first filler 30 during curing reaction, it is like embedding the second filler 40 on the first filler 30.

Table 1 below illustrates an exemplary formulation of silicone according to a first embodiment.

TABLE 1

| Component | Amount |
|---|---|
| $1^{st}$ Component (10): vinyl terminated polydimethylsiloxane | 100 parts by weight |
| $2^{nd}$ Component (20): trimethylsiloxy terminated (50% methylhydrosiloxane)-dimethylsiloxane copolymer | 2 part by weight |
| Coupling Agent (50): allyltrimethoxysilane | 2 parts by weight |

TABLE 1-continued

| Component | Amount |
|---|---|
| $1^{st}$ Filler (30): fumed silica, with specific surface area, BET 220, product Aerosil R812S (Evonik Degussa GmbH) | 1 part by weight |
| $2^{nd}$ Filler (40): silver nanoparticles, with particle size about 150 nanometers [Product 47MN-0001] (Inframat Corp.) | 0.00025 parts by weight |
| Catalyst (60): 3-3.5 wt % of Platinum, 1,3-diethenyl-1,1,3,3-tetramethyldisiloxane complexes in vinyl terminated polydimethylsiloxane [Product SIP 6830.3, CAS:[68478-92-2] (Gelest Inc.) | 10 ppm by total weight |

Figure 4:
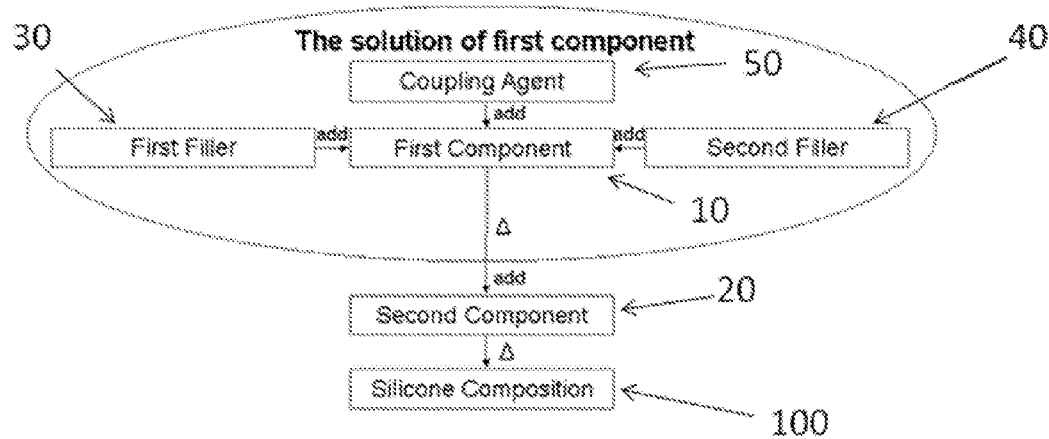
FIG. 4 illustrates an alternative embodiment of a process flow for producing silicone using a peroxide reaction.

FIG. 4 illustrates an alternative embodiment of a process flow for producing silicone 100 using a peroxide reaction. A portion of the reaction sequence is identical to the process illustrated in FIG. 1 and for this reason, similar element numbers are indicated for the first component 10, the first filler 30, the second filler 40, and the coupling agent 50. In this regard, the first filler 30 is added along with the second filler 40 to the first component. The coupling agent 50 is added and the solution is heated to a temperature with a range of about 100° C. to about 150° C. for several hours. Again, higher the temperature, the shorter the required time. In this second embodiment, the second component 20 is replaced by a peroxide, such as 2,5dimethyl-2,5di(t-butylperoxy)hexane, 2,4 dichlorobenzoyl peroxide, or dicumyl peroxide. The concentration of the second component 20 is within the range of 0.5 to 3% of the total weight of all components and fillers for the silicone composition. In this embodiment, there is no catalyst-need for the peroxide reaction. The mixture is heated to a temperature within the range of about 150° C. to about 200° C. for about one to three hours. Additional post-cure heating may be needed to ensure sufficient cross-linking to create the silicone composition.

TABLE 2

| Component | Amount |
|---|---|
| $1^{st}$ Component (10): vinyl terminated polydimethylsiloxane | 100 parts by weight |
| $2^{nd}$ Component (20): 50 wt % of 2,4-dichlorobenzoylperoxide in polydimethylsiloxane | 1 part by weight |
| Coupling Agent (50): allyltrimethoxysilane | 2 parts by weight |
| $1^{st}$ Filler (30): fumed silica, with specific surface area, BET 220, product Aerosil R812S (Evonik Degussa GmbH) | 1 part by weight |
| $2^{nd}$ Filler (40): silver nanoparticles, with particle size about 150 nanometers, product 47MN-0001 (Inframat Corp.) | 0.00025 parts by weight |

The effectiveness of the silicone formulation of Table 1 in resisting encrustation was evaluated in both in vitro and in vivo models. For example, artificial urine (in vitro) was prepared and tested with the silicone for encrustation along stainless steel, titanium, medical grade silicone (data normalized to this), and various compositions of the silicone described herein.

Example 1

In Vitro Testing

Artificial urine was produced by mixing equal amounts of Solution A and Solution B. The different compositions of each solution are given in Table 3 below. Chemicals were mixed in distilled water and allowed to dissolve thoroughly on a stirrer. The pH of each solution was approximately 6. After solutions were prepared, they were filtered with filters having 0.2 um pores.

TABLE 3

| Solution A (Gm/L) | Solution B (Mass) |
| --- | --- |
| $Na_2HPO_4$ (6.533) | $CaCl_2$ (1.765) |
| $(NH_4)2SO_4$ (5.338) | $K_3$Citrate (1.225) |
| $NH_4Cl$ (0.330) | $MgCl_2$ (1.220) |
| NaCl (17.24) | |
| KCl (11.23) | |
| $Na_2O_x$ (0.323) | |

Before use of the testing materials (silicone composition described herein, stainless steel, titanium, medical grade silicone), the materials were sterilized in 90% ethanol. Disks of all materials were strung on a monofilament suture in equally-spaced randomized positions. Medical grade silicone acted as the control disc in the center of each strand. Knots were tied before and after each disk to reduce possible interaction between materials. The strands with materials were then taped on one side of a 500-mL beaker across to the other side of the beaker. Two stands were hung at equal height, below the 400 mL mark on beaker, so that materials were exposed to equal amounts of artificial urine flow.

Once the strands were positioned in the beaker, a stir bar was placed inside the beaker and a piece of aluminum foil was securely placed on top of the beaker. The apparatus was then placed into the autoclave to sterilize the materials. After autoclaving the materials, under the hood, equal 1:1 proportions of Solution A and Solution B were mixed into the beaker so that all disks are fully immersed in the solutions. Aluminum foil on breaker was replaced and sealed tightly to prevent any contamination. The apparatus with artificial urine was then placed on a stirrer in a 5% $CO_2$ incubator at 37° C. to stimulate physiological conditions of the bladder. After one (1) week, under the hood, two strands with disks were removed and allowed to air dry.

Example 2

In Vivo Testing

In vivo encrustation tests were performed using a rabbit bladder model. The materials tested included standard medical grade silicone (MS), the new formulation silicone described herein with the formulation from Table 1 (PS), PS impregnated with 1% (by weight) of titanium oxide (PS—low Ti), PS impregnated with 3% (by weight) of titanium oxide (PS—high Ti), titanium (Ti), stainless steel (SS).

After institutional animal care and use committee approval, twenty (20) New Zealand white rabbits weighing 3 to 4 kg underwent anesthesia intramuscularly with a mixture of Xylazine (4 mg/kg) and Ketamine (30 mg/kg). Cystoscopy was preformed to guide 22 gauge needles into the bladder. The fine needles punctured the rabbit's bladder at the right and left lateral aspects of the dome. A monofilament suture was passed through the needles and needles were removed. Forceps were then fed through the cystoscope and ends of the suture were pulled through the urethra. Biomaterials were strung along one end of the suture with knots placed before and after each disk. Positions of materials on the suture were randomized and medical grade silicone was placed at the center to act as the control. Once all materials were strung, the ends of the suture were tied together and the discs were pulled back into the bladder. Rabbits were administered buprenorphine (0.05 mg/kg) to alleviate pain and allowed to recover. After one week, the rabbits were sacrificed and the disks were harvested.

Figure 5:
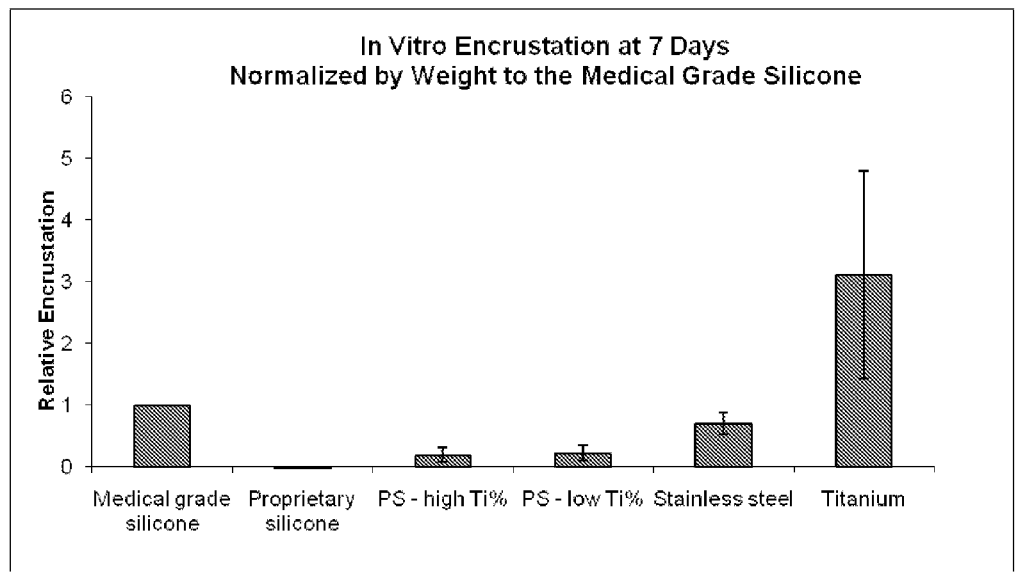
FIG. 5 illustrates the results of various biomaterials that were subject to seven days of in vitro encrustation. The results are normalized to medical grade silicone.
Figure 6:
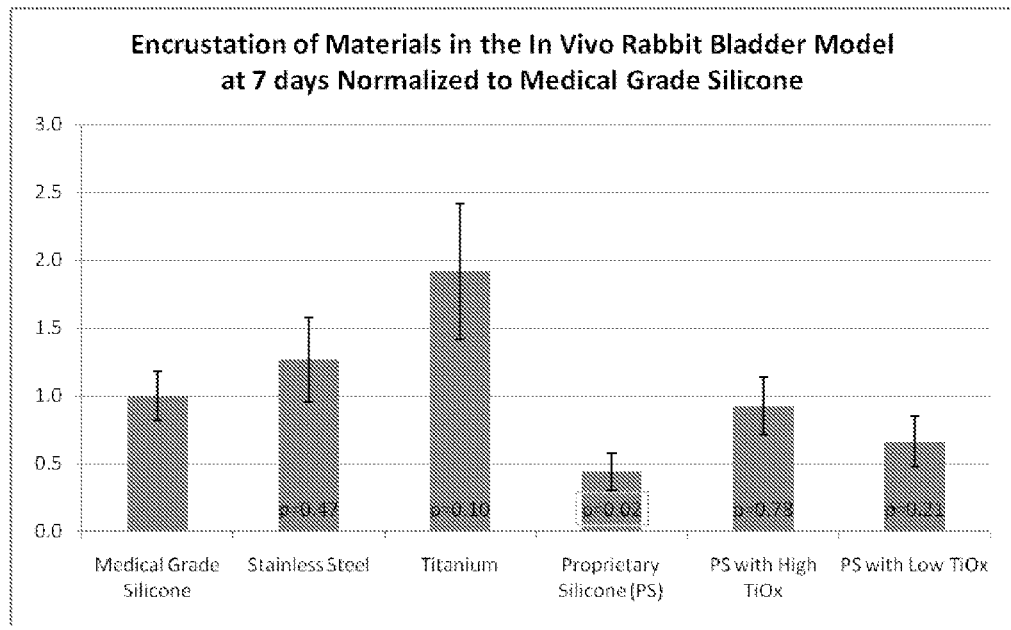
FIG. 6 illustrates the results of various biomaterials that were subject to seven days of in vivo encrustation. The results are normalized to medical grade silicone.

Encrustation Analysis:

Disks harvested from in vitro and in vivo experiments were allowed to air dry for 48 hours. Comparison of disk weights before and after the experiment was assessed to detect amount of encrustation. Relative amount of encrustation for each material was then normalized to the central medical grade silicone. Two-way statistical analysis was performed to determine if different biomaterials had a significant effect of encrustation. Results are presented as an average encrustation amount of three trials in vivo trails or twenty rabbits. FIG. 5 represents the results of in vitro encrustation experiments. FIG. 6 represents the results of in vivo encrustation experiments.

Figure 7:
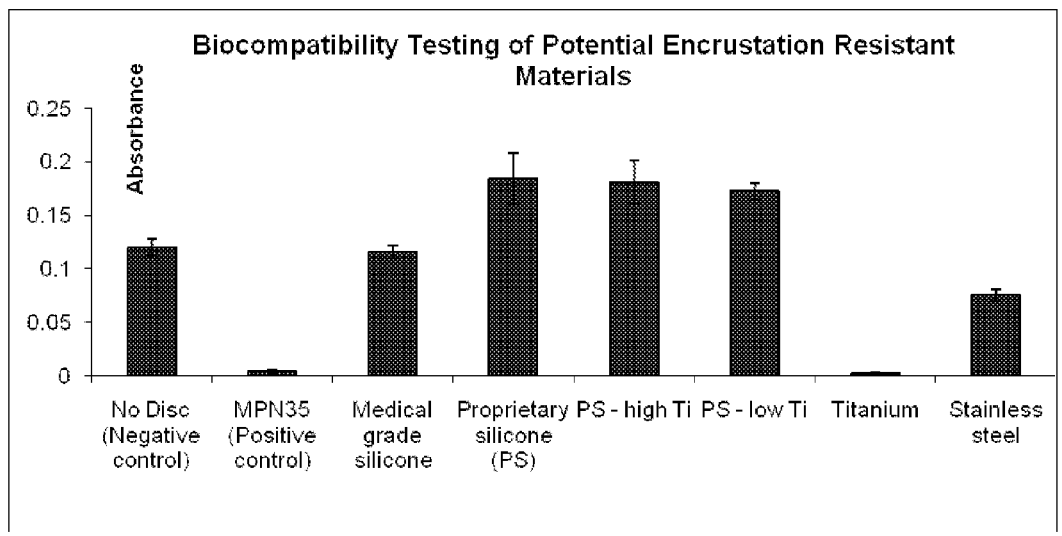
FIG. 7 illustrates the results of biocompatibility testing of various encrustation resistant materials.

Biocompatibility Testing:

Teu-2 cells, human urothelial cells, were grown in keratinocyte serum-free media (KSFM) with supplement (bovine pituitary extract plus recombinant epithelial growth factor). The cells were allowed to grow in an incubator with 5% $CO_2$ and 37° C. for three days. Cells were then treated with phosphate-buffered saline (PBS) and detached with trypsin. Trypsin inhibitor was added to inactivate the trypsin after cell detachment. The cells were centrifuged, resuspended in culture medium, and seeded at $5 \times 10^4$ cells per well in a 24 well plate with disks. Cells grown with no disk in the well or with MP35N were used as positive and negative controls, respectively. Previous use of MPN35 has shown that the material kills all cells in its presence. Cell vitality and proliferation was tested using MTT assay. Cells exposed to the different materials were incubated for 3 days. KSFM was removed from wells without disturbing the disks and fifty microliters of 3-(4,5-dimethylthiazol-2-yl)-2,5 diphenyltetrazolium bromide (MU) was added to each well. Three (3) hours of incubation was allowed for MTT cleavage to occur. After incubation, blue formazan product had formed. MTT solution was removed and isoproponal was added to lyse the cells. After 5 minutes, 0.2 milliliters of each well was transferred into 96-well plates for the biocompatibility assay. Using a Spectra Max Plus 384 microtiter plate meter the optical densities of culture medium were measured at 570 nm and subtraction of background absorbance at 690 nm. Samples with higher absorbance values indicate that fewer cells have been killed. FIG. 7 illustrates the results of the biocompatibility testing.

Results of the Encrustation And Biocompatibility Studies:

Differences in the amount of encrusted-on biomaterials in vitro and in vivo were present in one week. As each solution of artificial urine or rabbit model produced a variable amount of encrustation each sample disk's encrustation was normalized by a central silicone disk (medical grade silicone). The mean encrustation for each material, normalized and calculated from three in vitro trials is presented in FIG. 5. Dry weight analysis revealed that medical grade silicone and the silicone composition described herein had the least encrustation (p<0.01), whereas titanium alloy, stainless steel, and PS impregnated with titanium oxide had no statistical difference in the amount of encrustation formed.

In vivo experiments were replicated twelve times and the normalized mean encrustation of materials is summarized in FIG. 6. Rabbit model data verified in vitro results that the silicone composition described herein has a significantly less encrustation than other materials tested (p=0.02). Strong composite-cell adhesions and colonization of cultured cells were clearly represented with MTT assay of medical grade silicone (MS), PS silicone, PS impregnated with 3% (by weight) titanium oxide (PS—high Ti), and PS impregnated with 1% (by weight) of titanium oxide (PS—low Ti) were tested. The results are illustrated in FIG. 7. Yet less promising were stainless steel and titanium alloy which exhibited significant cytotoxicity ($p<0.05$).

Figure 8:
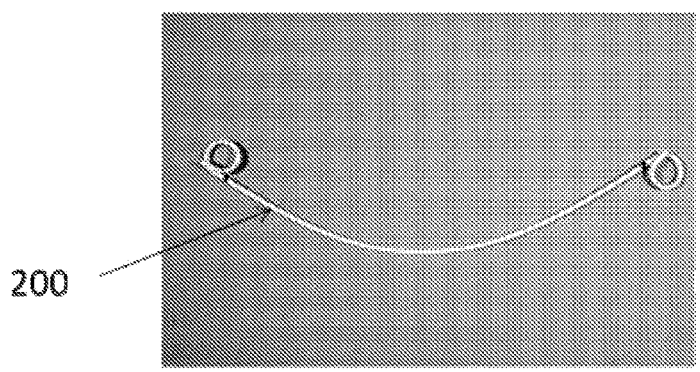
FIG. 8 illustrates one exemplary device (ureter stent) that may be made with the silicone described herein.
Figure 9:
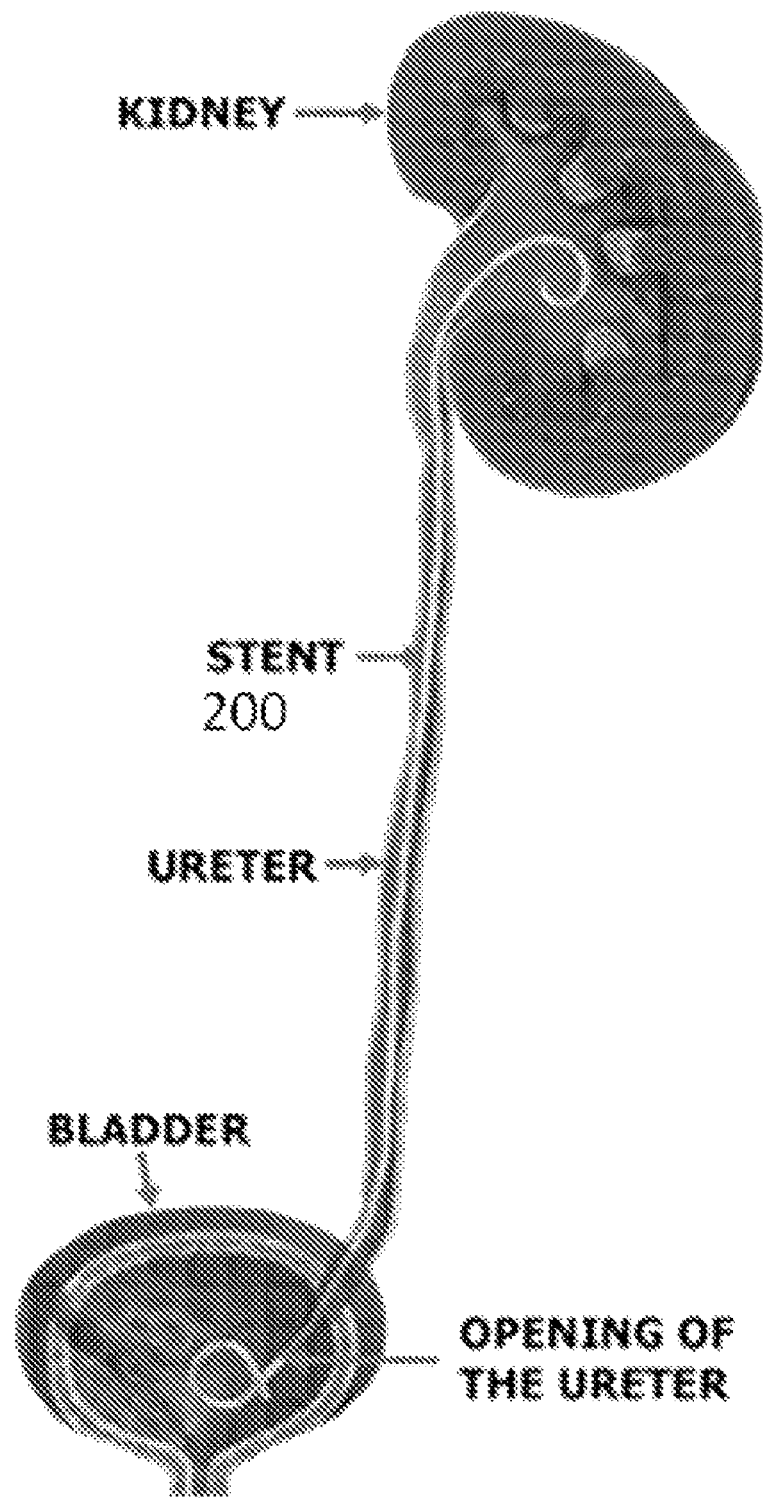
FIG. 9 illustrates placement of a ureter stent within the bladder, ureter, and kidney of a subject.

The silicone material 100 described herein may be used to form any number of medical devices. The silicone may also be used in medical tubing or other structures having lumen(s) in which resistance to encrustation is advantageous. FIG. 8 illustrates double-pigtail ureter stent 200 that may be made with the silicone described herein. FIG. 9 illustrates placement of a ureter stent 200 within the bladder, ureter, and kidney of a subject. While FIGS. 8 and 9 illustrate a medical device in the form of a ureter stent 200 it should be appreciated that the silicone material 100 described herein may be used in any number of devices where silicone may be useful and beneficial. Urinary stents are but one example of a device that can incorporate the silicone material 100.

While embodiments of the present invention have been shown and described, various modifications may be made without departing from the scope of the present invention. The invention, therefore, should not be limited, except to the following claims, and their equivalents.

What is claimed is:

1. A method of forming silicone having anti-microbial properties comprising:
   (a) adding silica and nanoparticles consisting essentially of silver to liquid vinyl-terminated polydimethylsiloxane;
   (b) adding a coupling agent to the mixture of (a) and heating the same, the coupling agent comprising trialkoxysilane having a formula $R^1Si(OR^2)_3$, wherein $R^1$ is vinyl or allyl, and $R^2$ is an alkyl radical having from 1 to 3 carbon atoms; and
   (c) adding trimethylsiloxy terminated polymethylhydrosiloxane to the mixture of (b) and subjecting the mixture to heat in the presence of a catalyst so as to cross-link and cure the same into a silicone elastomer.

2. The method of claim 1, wherein the nanoparticles comprise particles having diameters within the range of about 10 nm to about 200 nm.

3. The method of claim 1, wherein the concentration of the nanoparticles is less than 1000 ppm based on a total weight of all components of the silicone.

4. The method of claim 1, wherein the vinyl-terminated polydimethylsiloxane has a molecular weight of between 6,000 and 43,000.

5. The method of claim 1, wherein the vinyl-terminated polydimethylsiloxane has a viscosity between 100 and 3,500 cSt.

6. The method of claim 1, wherein the trimethylsiloxy terminated polymethylhydrosiloxane has a molecular weight between 900 and 2000.

7. The method of claim 1, wherein the trimethylsiloxy terminated polymethylhydrosiloxane has a viscosity between 15 and 35 cSt.

8. The method of claim 1, wherein the ratio of trimethylsiloxy terminated polymethylhydrosiloxane to (vinyl-terminated polydimethylsiloxane and trialkoxysilane) is within the range of 1.3:1 to 3.5:1 on a molar ratio basis.

9. The method of claim 1, wherein the coupling agent comprises allyltrimethoxysilane.

10. A method of forming silicone having anti-microbial properties comprising:
    (a) adding silica and nanoparticles consisting essentially of silver to liquid vinyl-terminated polydimethylsiloxane;
    (b) adding a coupling agent to the mixture of (a) and heating the same, the coupling agent comprising trialkoxysilane having a formula $R^1Si(OR^2)_3$, wherein $R^1$ is vinyl or allyl, and $R^2$ is an alkyl radical having from 1 to 3 carbon atoms; and
    (c) adding a peroxide to the mixture of (b) and subjecting the mixture to heat so as to cross-link and cure the same into a silicone elastomer.

11. The method of claim 10, wherein the peroxide comprises one of 2,5 dimethyl-2,5di(t-butylperoxy)hexane, 2,4dichlorobenzoyl peroxide, and dicumyl peroxide.

12. The method of claim 10, wherein the peroxide comprises between 0.5 and 3.0% of the total of weight of all components forming the silicone.

13. The method of claim 10, wherein the nanoparticles comprise particles having diameters within the range of about 10 nm to about 200 nm.

14. The method of claim 10, wherein the vinyl-terminated polydimethylsiloxane has a molecular weight of between 6,000 and 43,000.

15. The method of claim 1, wherein the vinyl-terminated polydimethylsiloxane has a viscosity between 100 and 3,500 cSt.

16. The method of claim 1, wherein the coupling agent comprises allyltrimethoxysilane.

17. The method of claim 1, wherein the catalyst is a solution of platinum-divinyltetramethyldisiloxane complex in vinyl terminated polydimethylsiloxane.

* * * * *